United States Patent
Swan

(10) Patent No.: US 10,898,379 B2
(45) Date of Patent: Jan. 26, 2021

(54) RETINAL TREATMENT

(71) Applicant: OPTOS PLC, Fife (GB)

(72) Inventor: Derek Swan, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 17 days.

(21) Appl. No.: 15/543,549

(22) PCT Filed: Jan. 26, 2016

(86) PCT No.: PCT/GB2016/050163
§ 371 (c)(1),
(2) Date: Jul. 13, 2017

(87) PCT Pub. No.: WO2016/120607
PCT Pub. Date: Aug. 4, 2016

(65) Prior Publication Data
US 2017/0367889 A1    Dec. 28, 2017

(30) Foreign Application Priority Data
Jan. 26, 2015 (GB) .................................. 1501274.3

(51) Int. Cl.
*A61F 9/008* (2006.01)
*A61B 3/12* (2006.01)

(52) U.S. Cl.
CPC ............ *A61F 9/00821* (2013.01); *A61B 3/12* (2013.01); *A61F 2009/00863* (2013.01); *A61F 2009/00878* (2013.01); *A61F 2009/00897* (2013.01)

(58) Field of Classification Search
CPC ....................... A61F 9/008–2009/00897; A61B 18/20–18/28; A61N 5/06–2005/073
(Continued)

(56) References Cited

U.S. PATENT DOCUMENTS 7,959,290 B2 * 6/2011 Cairns .................. A61B 3/1225
                                                      351/206
2007/0129775 A1    6/2007 Mordaunt et al.
(Continued)

FOREIGN PATENT DOCUMENTS

JP    2012-135550 A    7/2012
JP    2014-121606      7/2014
(Continued)

OTHER PUBLICATIONS

International Preliminary Report on Patentability for PCT/GB2016/050163 dated Aug. 10, 2017.
(Continued)

*Primary Examiner* — Jonathan T Kuo
(74) *Attorney, Agent, or Firm* — Foley & Lardner LLP

(57) ABSTRACT

A method of determining control parameters of a retinal treatment system comprising acquiring an image of a retina of a subject's eye using an imaging laser and an optical system of the retinal treatment system, presenting an image of the retina to a user of the retinal treatment system, receiving from the user location data of the retinal image that locates at least one treatment site of the retina, receiving from the user a required laser light pattern for use on the treatment site, using the location data to determine a location control parameter which causes the optical system to direct laser light from a treatment laser of the retinal treatment system to the treatment site, and using the required laser light pattern to determine a pattern control parameter which causes the treatment laser to produce a laser light pattern which passes through the optical system and results in the required laser light pattern at the treatment site.

12 Claims, 2 Drawing Sheets

Figure 1:
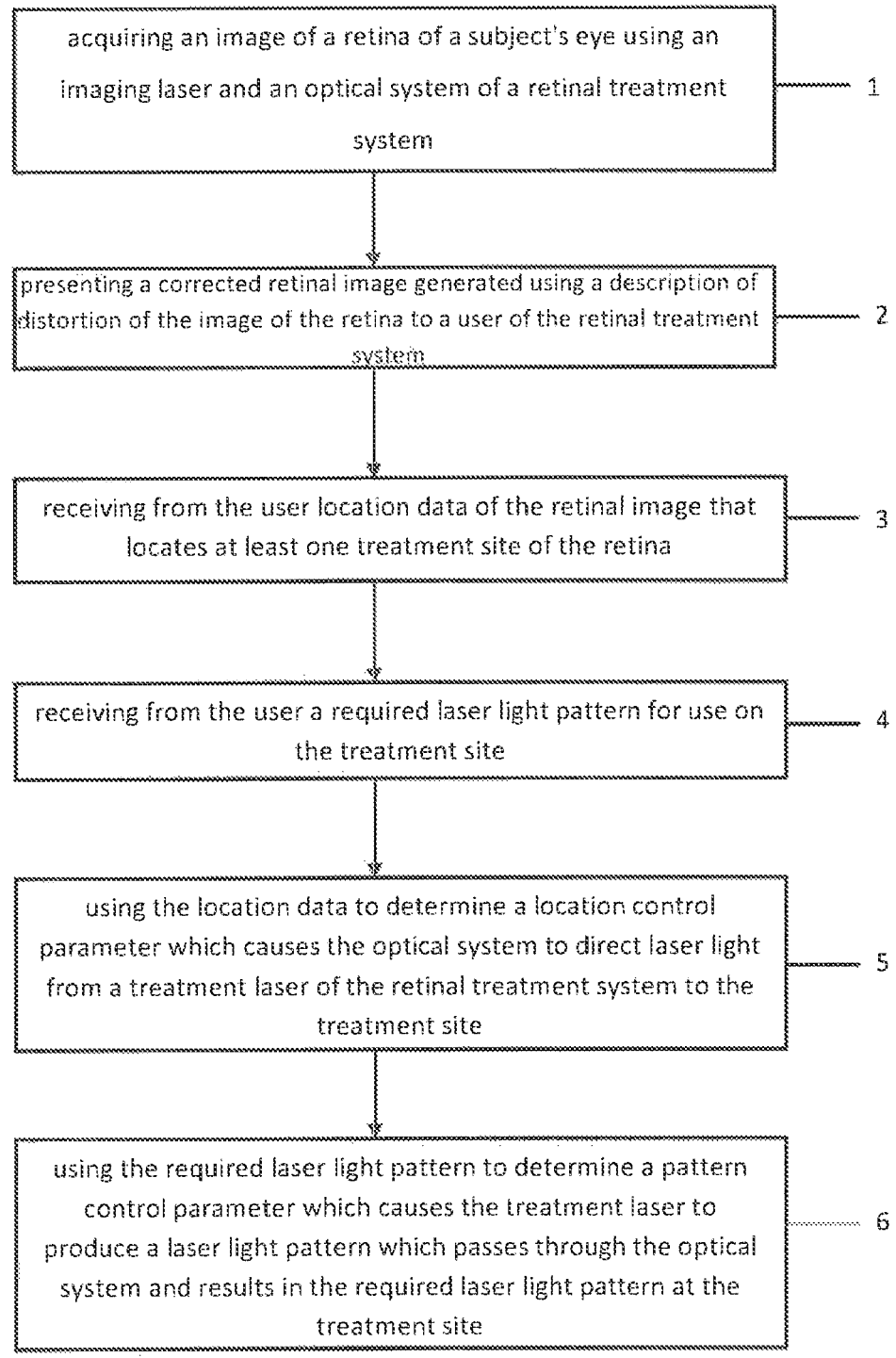

(58) Field of Classification Search
USPC .............................................. 606/4–6, 10–12
See application file for complete search history.

(56) References Cited

U.S. PATENT DOCUMENTS

| | | | |
|---|---|---|---|
| 2007/0252951 A1* | 11/2007 | Hammer | A61F 9/008 |
| | | | 351/221 |
| 2008/0001553 A1 | 1/2008 | Qiu et al. | |
| 2008/0015553 A1 | 1/2008 | Zacharias | |
| 2010/0141895 A1* | 6/2010 | Cairns | A61B 3/1225 |
| | | | 351/206 |
| 2010/0150415 A1 | 6/2010 | Atkinson et al. | |
| 2012/0095349 A1 | 4/2012 | Peyman | |
| 2012/0184857 A1 | 7/2012 | Yokosuka | |
| 2015/0371383 A1* | 12/2015 | Chabrier | A61B 3/12 |
| | | | 600/427 |

FOREIGN PATENT DOCUMENTS

| | | |
|---|---|---|
| JP | 2014-217755 | 11/2014 |
| JP | 2015-008841 A | 1/2015 |
| WO | WO-2014/096835 | 6/2014 |
| WO | WO 2014106536 A2 * | 7/2014 |
| WO | WO-2014/172641 | 10/2014 |

OTHER PUBLICATIONS

International Search Report for PCT/GB2016/050163 dated May 10, 2016.
Search Report for GB1601456.5 dated Jul. 11, 2016.
Notice of Reasons for Rejection for Application No. 2017-538212 dated Jul. 30, 2019.
Notice of Reasons for Rejection for Application No. 2017-538212 dated Apr. 7, 2020.

* cited by examiner

RETINAL TREATMENT

RELATED APPLICATIONS

This application is a national stage application of International Patent Application Number PCT/GB2016/050163, which application claims priority to United Kingdom Patent Application GB 1501274.3. International Patent Application Number PCT/GB2016/050163 and United Kingdom Patent Application GB 1501274.3 are incorporated by reference.

The invention relates to improvements in retinal treatment, particularly retinal photocoagulation treatment, combining improved imaging of the retina and treatment of the retina.

Retinal photocoagulation is used for treating vascular and structural abnormalities in a subject's retina and choroid. Recently, patterned laser photocoagulation systems have been made available whereby spot size and pattern of the photocoagulation laser may be predefined by a user, such as a physician. This enables the user to apply a selected pattern of laser-induced photocoagulation to the subject's retina, improving precision, comfort and speed of the photocoagulation process. However, care needs to be taken in the choice of retinal location for the photocoagulation process and in the laser pattern chosen. This requires the user to have as much information as possible about the retina of the subject, provided for example in an image of the retina.

According to a first aspect of the invention there is provided a method of determining control parameters of a retinal treatment system comprising
(i) acquiring an image of a retina of a subject's eye using an imaging laser and an optical system of the retinal treatment system,
(ii) presenting an image of the retina to a user of the retinal treatment system,
(iii) receiving from the user location data of the retinal image that locates at least one treatment site of the retina,
(iv) receiving from the user a required laser light pattern for use on the treatment site,
(v) using the location data to determine a location control parameter which causes the optical system to direct laser light from a treatment laser of the retinal treatment system to the treatment site, and
(vi) using the required laser light pattern to determine a pattern control parameter which causes the treatment laser to produce a laser light pattern which passes through the optical system and results in the required laser light pattern at the treatment site.

It will be appreciated that the order of the steps of the method can be changed and additional steps may be added.

The method of determining control parameters of a retinal treatment system may further comprise
receiving a description of distortion of the retinal image, using the distortion description to generate a corrected retinal image,
presenting the corrected retinal image to a user of the retinal treatment system,
receiving from the user location data of the corrected retinal image that locates at least one treatment site of the retina,
using the distortion description with the location data to determine a location control parameter which causes the optical system to direct laser light from the treatment laser to the treatment site,
using the distortion description with the required laser light pattern to determine a pattern control parameter which causes the treatment laser to produce a laser light pattern which passes through the optical system and results in the required laser light pattern at the treatment site.

Acquiring the image of the retina of a subject's eye may comprise using an ultra-wide field scanning laser ophthalmoscope comprising the imaging laser and optical system of the retinal treatment system. The optical system may comprise optical elements and a detector. The optical elements may comprise a first scan element, a first scan transfer element, a second scan element and a second scan transfer element.

Ultra-wide field scanning laser ophthalmoscopes are available that allow imaging of the fundus to the far periphery in an undilated examination of a subject's retina. The resultant wide field images of the retina give enhanced visualization of the extent of disease in the subject retina and can be used to enhance the determination of the location of a treatment site and the optimum laser light pattern used in photocoagulation treatment of the site.

Presenting the retinal image or the corrected retinal image to a user of the retinal treatment system may comprise presenting the image on a visual display unit of the retinal treatment system.

Receiving the location data from the user may comprise receiving the data from an annotation of the retinal image or the corrected retinal image. Receiving the location data from the user may comprise receiving the data as coordinates of the retinal image or the corrected retinal image.

Receiving the required laser pattern from the user may comprise receiving the pattern from an annotation of the retinal image or the corrected retinal image. Receiving the required laser pattern from the user may comprise receiving the pattern as coordinates of the retinal image or the corrected retinal image. Receiving the required laser pattern from the user may comprise receiving the pattern as coordinates of the retinal image or the corrected retinal image for a distribution of laser spots making up the pattern.

The location control parameter may comprise a location control signal for the optical system. The location control signal may be used to configure the optical system to place a first scan element and a second scan element of the optical system in positions which direct the laser light from the treatment laser to the treatment site.

The pattern control parameter may comprise a pattern control signal for the treatment laser. The pattern control signal may be used to configure the treatment laser to produce a laser light pattern which, on passing through the optical system, results in the required laser light pattern at the treatment site.

The distortion description of the retinal image may be derived using an optical system model based method for determining distortion. The distortion description of the retinal image may be derived using a target based method for determining distortion. The distortion description may be in the form of a look-up table or an equation. The distortion of the retinal image may be caused by distortion introduced by the optical system and/or the eye.

The method may comprise outputting the location control parameter and the pattern control parameter for use to treat the treatment site of the retina. The method may comprise storing the location control parameter and the pattern control parameter for use to treat the treatment site of the retina.

According to a second aspect of the invention there is provided a retinal treatment system comprising
(i) an imaging laser and an optical system which acquire an image of the retina of a subject's eye, (ii) a presentation module which presents the retinal image to a user of the system, (iii) an input module which receives from the user location data of the retinal image that locates at least one treatment site of the retina and a required laser light pattern for use on the treatment site, (iv) a control parameter processor which uses the location data to determine a location control parameter and which uses the required laser light pattern to determine a pattern control parameter, (v) a treatment laser which directs laser light through the optical system onto the retina, and (vi) a controller which receives the location control parameter and the pattern control parameter and configures the optical system to direct laser light from the treatment laser to the treatment site, and configures the treatment laser to produce a laser light pattern which passes through the optical system and results in the required laser light pattern at the treatment site.

The input module may receive a description of distortion of the retinal image. The input module may use the distortion description to generate a corrected retinal image. The presentation module may present the corrected retinal image to a user of the retinal treatment system. The input module may receive from the user location data of the corrected retinal image that locates at least one treatment site of the retina. The control parameter processor may use the distortion description with the location data to determine the location control parameter. The control processor may use the distortion description with the required laser light pattern to determine the pattern control parameter.

The retinal treatment system may comprise an ultra-wide field scanning laser ophthalmoscope which comprises the imaging laser and optical system. The optical system may comprise optical elements and a detector. The optical elements may comprise a first scan element, a first scan transfer element, a second scan element and a second scan transfer element.

The presentation module of the retinal treatment system may comprise a visual display unit.

Figure 2:
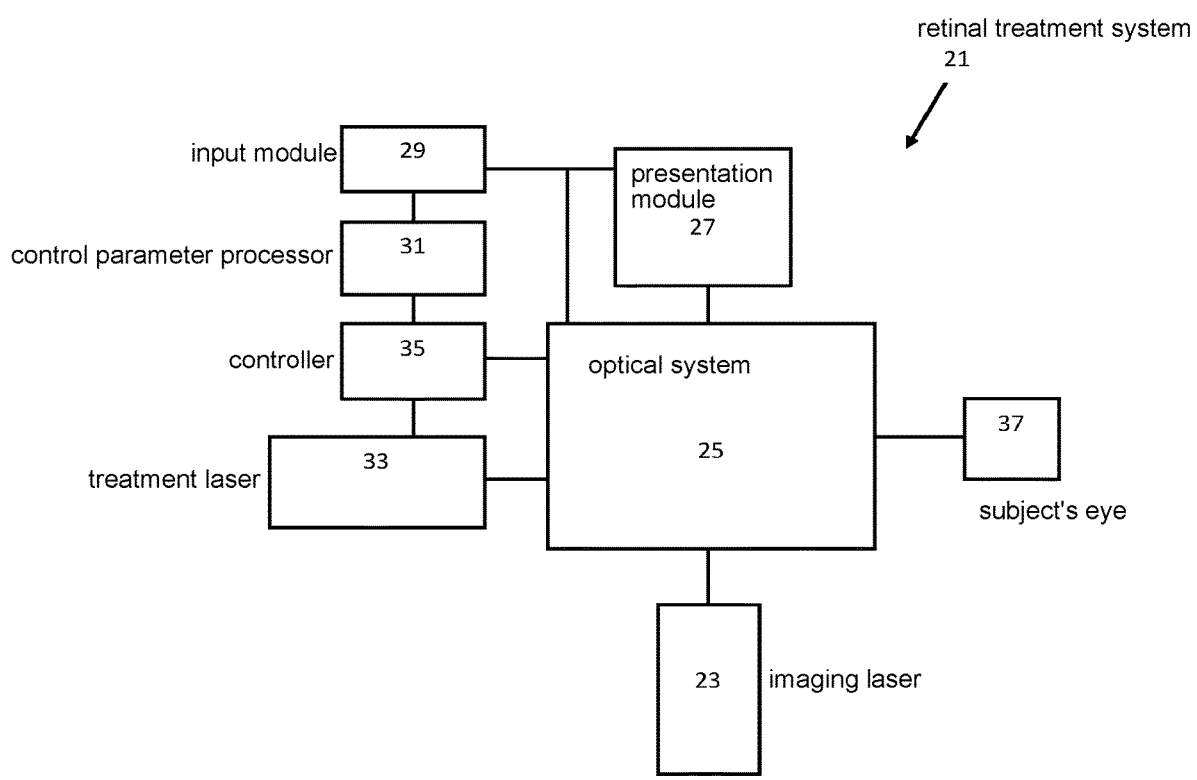

An embodiment of the invention will now be described by way of example only, with reference to the accompanying drawings, in which:

FIG. 1 is a flow chart illustrating a method of determining control parameters of the retinal treatment system according to the first aspect of the invention, and FIG. 2 is a schematic representation of a retinal treatment system according to the second aspect of the invention.

Referring to FIG. 1, the method of determining control parameters of a retinal treatment system comprises the steps of acquiring an image of a retina of a subject's eye using an imaging laser and an optical system of the retinal treatment system (1), presenting an image of the retina to a user of the retinal treatment system (2), receiving from the user location data of the retinal image that locates at least one treatment site of the retina (3), receiving from the user a required laser light pattern for use on the treatment site (4), using the location data to determine a location control parameter which causes the optical system to direct laser light from a treatment laser of the retinal treatment system to the treatment site (5), and using the required laser light pattern to determine a pattern control parameter which causes the treatment laser to produce a laser light pattern which passes through the optical system and results in the required laser light pattern at the treatment site (6).

Referring to FIG. 2, the retinal treatment system 21 comprises an imaging laser 23, an optical system 25, a presentation module 27, an input module 29, a control parameter processor 31, a treatment laser 33 and a controller 35.

The imaging laser 23 and the optical system 25 form an ultra-wide field scanning laser ophthalmoscope. The optical system 25 comprises optical elements, comprising a first scan element, a first scan transfer element, a second scan element, a second scan transfer element, and a detector (all not shown). The imaging laser 23 emits a laser beam which passes through the optical system and onto the retina of a subject's eye 37. Light from the retina passes back through the optical system and is detected by a detector (not shown) which forms an image of the retina. The use of an ultra-wide field scanning laser ophthalmoscope allows imaging of the retina to its far periphery, and the resultant wide field retinal image gives enhanced visualization of the extent of disease in the subject retina.

The input module 29 comprises a reader for a memory device. In this embodiment, the input module 29 receives a description of distortion of the retinal image from a memory device. The image distortion is caused by distortion introduced by the optical system 25 and the subject's eye 37. The input module 29 further comprises a processor which uses the distortion description to generate a corrected retinal image. The input module 29 passes the corrected retinal image to the presentation module 27.

The presentation module 27 comprises a visual display unit (not shown). The visual display unit presents the corrected retinal image to a user of the retinal treatment system. The user uses the visual display unit and a marking device (not shown), such as a mouse or a pen, to annotate the corrected retinal image. The corrected retinal image is annotated to indicate location data that locates at least one treatment site of the retina and to indicate a required laser light pattern for use on the treatment site. The presentation module 27 passes the location data and the required laser light pattern to the input module 29.

The input module 29 passes the location data and the required laser light pattern and the description of the distortion to the control parameter processor 31. The control parameter processor 31 uses the distortion description with the location data to determine the location control parameter. The control parameter processor 31 also uses the distortion description with the required laser light pattern to determine the pattern control parameter. The control parameter processor 31 passes the location control parameter and the pattern control parameter to the controller 35.

The location control parameter comprises a location control signal for the optical system 25. On receipt of the location control signal by the controller 35, the controller 35 uses the location control signal to configure the optical system 25 to place a first scan element and a second scan element of the optical system 25 in positions which direct the laser light from the treatment laser 33 to the treatment site. The pattern control parameter comprises a pattern control signal for the treatment laser 33. On receipt of the pattern control signal by the controller 35, the controller 35 uses the pattern control signal to configure the treatment laser 33 to produce a laser light pattern which on passing through the optical system 25, results in the required laser light pattern at the treatment site.

Thus the treatment laser 33 directs laser light in a required patterns to a location of the treatment site on the retina of the subject's eye 37, and can be used for treatment of the site for example by photocoagulation.

In this embodiment, distortion of the optical system 5 and the subject's eye is accounted for. It will be appreciated, however, that this may not be the case. In this embodiment, the input module 9, the control parameter processor 11 and the controller 15 are shown as separate modules. It will be appreciated that these can be comprised in the same module and can be realised as hardware or software or a combination of hardware and software.

The invention claimed is:

1. A method of determining control parameters of a retinal treatment system comprising:
    acquiring an image of a retina of a subject's eye using an imaging laser and an optical system of the retinal treatment system;
    receiving a description of distortion of the image of the retina;
    using the distortion description to generate a corrected retinal image;
    presenting the corrected retinal image to a user of the retinal treatment system;
    receiving from the user location data of the corrected retinal image that locates at least one treatment site of the retina;
    receiving from the user a required laser light pattern for use on the treatment site;
    using the distortion description with the location data to determine a location control parameter which causes the optical system to direct laser light from a treatment laser of the retinal treatment system to the treatment site; and
    using the distortion description with the required laser light pattern to determine a pattern control parameter which configures the treatment laser to produce a corresponding laser light pattern which, having passed through the optical system, results in the required laser light pattern at the treatment site.

2. A method according to claim 1, in which acquiring the image of the retina of a subject's eye comprises using an ultra-wide field scanning laser ophthalmoscope comprising the imaging laser and optical system of the retinal treatment system.

3. A method according to claim 1, in which receiving the location data from the user comprises receiving the location data as coordinates of the retinal image or the corrected retinal image.

4. A method according to claim 1, in which receiving the required laser light pattern from the user comprises receiving the laser light pattern from an annotation of the retinal image or the corrected retinal image.

5. A method according to claim 1, in which receiving the required laser light pattern from the user comprises receiving the laser light pattern as coordinates of the retinal image or the corrected retinal image.

6. A method according to claim 1, in which the location control parameter comprises a location control signal for the optical system.

7. A method according to claim 6, in which the location control signal is used to configure the optical system to place a first scan element and a second scan element of the optical system in positions which direct the laser light from the treatment laser to the treatment site.

8. A method according to claim 1, in which the pattern control parameter comprises a pattern control signal for the treatment laser.

9. A method according to claim 8, in which the pattern control signal is used to configure the treatment laser to produce the corresponding laser light pattern.

10. A method according to claim 1, further comprising any of outputting or storing the location control parameter and the pattern control parameter for use to treat the treatment site of the retina.

11. A retinal treatment system comprising:
    an imaging laser and an optical system arranged to acquire an image of the retina of a subject's eye; and
    one or more processors configured to
        receive a description of distortion of the image of the retina;
        use the distortion description to generate a corrected retinal image;
        present the corrected retinal image to a user of the system;
        receive from the user location data of the corrected retinal image that locates at least one treatment site of the retina, and a required laser light pattern for use on the treatment site;
        use the distortion description with the location data to determine a location control parameter; and
        use the distortion description with the required laser light pattern to determine a pattern control parameter;
    a treatment laser arranged to direct laser light through the optical system onto the retina; and
    wherein the one or more processors is further configured to
        receive the location control parameter and the pattern control parameter;
        configure the optical system to direct laser light from the treatment laser to the treatment site; and
        configure, using the pattern control parameter, the treatment laser to produce a corresponding laser light pattern which, having passed through the optical system, results in the required laser light pattern at the treatment site.

12. A system according to claim 11, comprising an ultra-wide field scanning laser ophthalmoscope which comprises the imaging laser and optical system.

* * * * *